(12) United States Patent
Ackerman

(10) Patent No.: US 6,827,703 B1
(45) Date of Patent: Dec. 7, 2004

(54) SINGLE LUMEN BALLOON CATHETER APPARATUS

(75) Inventor: Bernard Ackerman, Metuchen, NJ (US)

(73) Assignee: CooperSurgical, Inc., Trumbull, CT (US)

( * ) Notice: Subject to any disclaimer, the term of this patent is extended or adjusted under 35 U.S.C. 154(b) by 0 days.

(21) Appl. No.: 09/449,096

(22) Filed: Nov. 24, 1999

(51) Int. Cl.$^7$ .......................... A61M 29/00; A61M 5/00
(52) U.S. Cl. ............................ 604/96.01; 604/99.01; 604/99.03; 604/99.04; 604/247; 600/433; 600/435
(58) Field of Search .................... 604/509, 514–515, 604/96.01, 97.01–97.03, 98.01–98.02, 99.01–99.04, 523, 247, 103.77; 606/193, 194, 192, 108; 600/431–435, 6, 427, 135

(56) References Cited

U.S. PATENT DOCUMENTS

| | | | |
|---|---|---|---|
| 3,926,705 A | | 12/1975 | Todd |
| 3,983,879 A | | 10/1976 | Todd |
| 4,089,337 A | | 5/1978 | Kronner |
| 4,349,033 A | | 9/1982 | Eden |
| 4,430,076 A | | 2/1984 | Harris |
| 4,489,732 A | | 12/1984 | Hasson |
| 4,921,479 A | * | 5/1990 | Grayzel ...................... 604/509 |
| 5,100,382 A | * | 3/1992 | Valtchev ................ 604/102.02 |
| 5,147,335 A | | 9/1992 | Wright |
| 5,259,836 A | | 11/1993 | Thurmond et al. |
| 5,423,745 A | * | 6/1995 | Todd et al. .................. 604/500 |
| 5,540,658 A | | 7/1996 | Evans et al. |
| 5,624,399 A | * | 4/1997 | Ackerman ............. 604/103.03 |
| 5,707,358 A | * | 1/1998 | Wright ................... 604/103.07 |
| 6,458,096 B1 | * | 10/2002 | Briscoe et al. ........... 604/96.01 |

* cited by examiner

*Primary Examiner*—Nicholas D. Lucchesi
*Assistant Examiner*—Catherine S. Williams
(74) *Attorney, Agent, or Firm*—Lathrop & Gage, L.C.

(57) ABSTRACT

A catheter useful for non-surgical entry into a uterus to dispense a diagnostic fluid therein. The catheter includes a tubular body having a lumen extending from a first end thereof to a second end thereof. The lumen includes an external opening adjacent the first end for dispensing a diagnostic fluid into the interior of a subject uterus, and a balloon disposed marginally adjacent to the first end of the body for fluid sealing the interior of the subject uterus. The lumen further includes a second opening in fluid communication with the interior of the balloon for inflation thereof with the diagnostic fluid. In most applications, the catheter can be combined with a syringe to form a catheter apparatus.

2 Claims, 2 Drawing Sheets

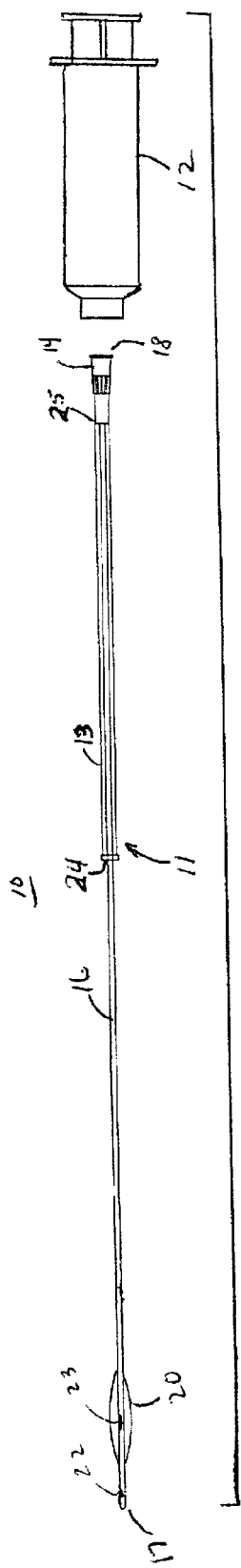
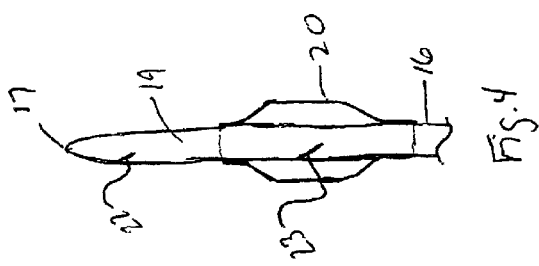

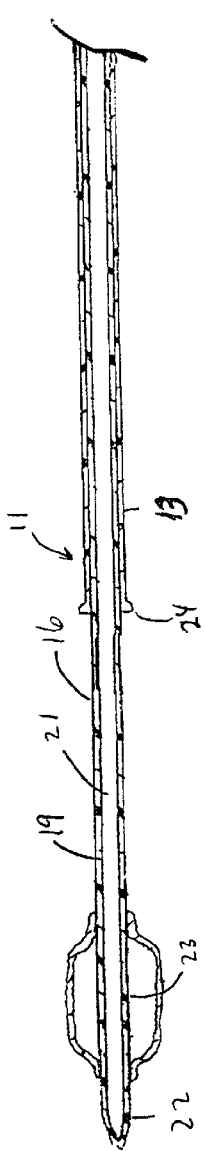
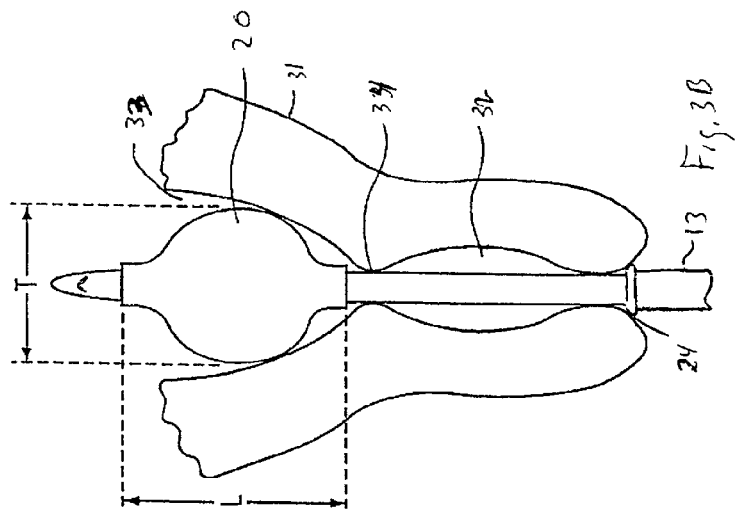
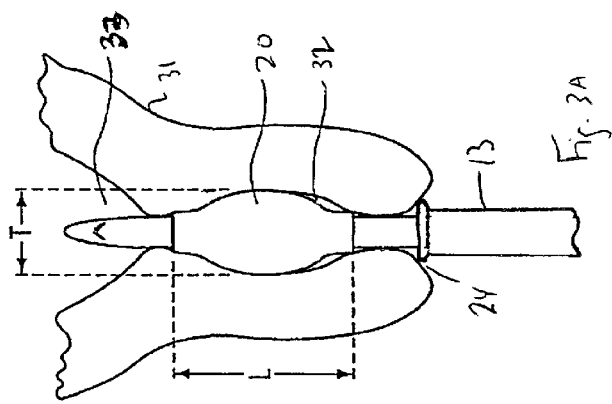

SINGLE LUMEN BALLOON CATHETER APPARATUS

FIELD OF THE INVENTION

The present invention relates to catheters, and in particular, to a balloon-bearing single lumen catheter for injecting diagnostic fluids into a body cavity and a catheter apparatus employing same.

BACKGROUND OF THE INVENTION

Diagnostic procedures which require a non-surgical entry into the uterus are well known. One such procedure known as hysterosalpingography, is a radiographic method for imaging the anatomical structures of the uterus and fallopian tubes. Hysterosalpingography involves inserting a fine flexible catheter through the cervical canal and injecting a contrast medium, such as an iodinated fluid, into the uterus. Radiography is then carried out to provide imaging information pertaining to the subject uterus.

Another well known diagnostic procedure which entails the non-surgical entry into the uterus is called hysterosonography. This procedure also employs a fine flexible catheter that is inserted into the cervical canal of the uterus. The catheter in this procedure enables the physician or technician to inject a sterile saline solution into the uterus to expand it so that an ultrasound scanner can be used to sonographically observe the uterus.

The catheters used in both procedures typically have means for sealing off the uterus after injection of the fluid to prevent backflow into the vaginal canal. One such means includes an inflatable intrauterine balloon made from an elastomeric material disposed adjacent the distal tip of the catheter. The catheter includes a first lumen that communicates with the interior of the balloon to enable inflation and deflation with an inflation syringe, and second lumen that is open at the distal tip of the catheter to enable injection of a desired diagnostic fluid into the uterus with a injection syringe.

The balloon catheter is operated by inserting the distal tip thereof through the cervical canal and into the uterus with the intrauterine balloon deflated. The insertion of the distal tip operates to position the deflated intrauterine balloon in the uterus or cervical canal. Once positioned, the inflation syringe is used to inflate the intrauterine balloon with air to seal block the cervical canal and the injection syringe is used to inject the desired diagnostic fluid into the uterus.

One problem associated with balloon catheters of this design is that they are relatively expensive to manufacture because they include two lumens and double syringes. Therefore, a less expensive balloon-bearing catheter is needed.

SUMMARY OF THE INVENTION

A catheter used for non-surgically entry into a uterus to dispense a diagnostic fluid therein; the catheter comprising a tubular body having a lumen extending from a first end thereof to a second end thereof. The lumen includes an external opening adjacent the first end for dispensing a diagnostic fluid into the interior of a subject uterus, and a balloon disposed marginally adjacent to the first end of the body for fluid sealing the interior of the subject uterus. The lumen further includes a second opening in fluid communication with the interior of the balloon for inflation thereof with the diagnostic fluid.

The catheter is typically combined with a syringe to form a catheter apparatus if desired.

BRIEF DESCRIPTION OF THE DRAWINGS

The advantages, nature, and various additional features of the invention will appear more fully upon consideration of the illustrative embodiments now to be described in detail in connection with accompanying drawings wherein:

FIG. 1 is an elevational view of a catheter apparatus according to an embodiment of the invention;

FIG. 2 is a sectional view of the catheter of the apparatus;

FIG. 3A is a diagrammatic view of the catheter of the invention anchored in the cervical canal of a subject uterus;

FIG. 3B is a diagrammatic view of the catheter of the invention anchored in the uterine cavity of a subject uterus; and FIG. 4 is an enlarged diagrammatic view of the distal portion of the catheter of the invention.

It should be understood that the drawings are for purposes of illustrating the concepts of the invention and are not necessarily to scale.

DETAILED DESCRIPTION OF THE INVENTION

FIG. 1 shows a catheter apparatus according to an embodiment of the invention. The catheter apparatus 10 is an inline assembly comprised of a flexible, single lumen catheter 11 and a conventional syringe 12. The catheter apparatus 10 is primarily intended for non-surgical entry into the uterine cavity, however, one of ordinary skill in the art will recognize its usefulness in other related procedures.

The catheter 11 of the apparatus 10 includes a flexible tubular body 16 which is preferably made from a clear polyurethane or like material. The body 16 has a distal end 17 and proximal end 18 and is threadedly disposed in a semi-rigid sheath 13 which is preferably made from polypropylene or any other suitable material. The sheath 13 has a distal end 24, a proximal end 25, and a length which is about 40% percent less than the length of the catheter body 16. The sheath 13 can be slidably moved back and forth along the catheter body 16 to uncover the distal portion of the body 16 to allow it to bend and flex freely or to cover it to prevent bending and flexing in the vagina thus aiding the insertion of the catheter 11 in the cervical canal. A conventional female Luer hub connector 14 is provided at the proximal end 18 of the catheter body 16 for detachably fluid coupling the syringe 12 (which should be equipped with a male Luer connector) to the catheter 11. An inflatable balloon 20 (shown in the deflated state) is affixed to and encloses a marginal distal end portion of the body 16. The balloon 20 can be of the type described in U.S. Pat. No. 5,624,399 issued to Bernard Ackerman the disclosure of which is incorporated herein by reference.

The balloon 20 taught in U.S. Pat. No. 5,624,399 is typically constructed from an elastomeric material such as polyurethane or any other elastomeric material having a Shure A durometer of between approximately 70 and 95. U.S. Pat. No. 5,624,399 further teaches attaching the balloon 20 to the body 16 so that its longitudinal axis L is longer than its transverse axis T upon initial inflation thereof. This allows the balloon 20 to be progressively transformed from an ellipsoidal shape to a spherical shape with increasing inflation pressure. The balloon 20 in the ellipsoidal shape as shown in FIG. 3A, can be used for occluding the cervical canal 32 of a subject uterus 31 thus preventing obstruction of the uterus 31 during imaging. If pain and/or cramping is experienced with the balloon 20 in the cervical canal 32, it can be moved into the uterine cavity 33 of the subject uterus 31 and further expanded into the spherical shape to block the internal opening 34 of the cervical canal 32 as shown in FIG. 3B to obviate the pain and/or cramping.

It should be understood that other embodiments of the invention can employ more conventional balloon designs. Such balloon designs typically inflate into a spherical shape and are made from latex.

FIG. 2 shows a cross-sectional view through the catheter 11 of the apparatus 10. As can be seen, the body 16 of the catheter 11 is constructed with a single lumen 21 that extends virtually the entire length thereof. The wall 19 of the lumen 21 includes a first slit 22 (best shown in FIG. 4) adjacent to the distal end 17 of the body 16. The first slit 22 allows the lumen 21 to communicate with the external environment to provide a fluid communication path for injecting a diagnostic fluid such as saline or a contrast dye into a the uterine cavity of a subject uterus. The lumen 21 also communicates with the interior of balloon 20 via a second slit 23 (best shown in FIG. 4) provided in the wall 19 of the lumen 21. The second slit 23 is equal to or up to 28 percent larger in area than the first slit 22 to provide a communication path for inflating the balloon 20 with diagnostic fluid as will be explained further on. In other embodiments of the invention, either one or both of the slits 22, 23 can be replaced with a correspondingly placed aperture(s).

The apparatus 10 is typically operated by moving the sheath 13 toward the distal end 17 of the catheter 11, to cover the most of the distal portion of the catheter body 16 (the balloon 20 should be deflated). The catheter 11 is then inserted into the vaginal canal so that the distal end 17 of the catheter 11 just enters the cervical canal of a subject uterus and the distal end 24 of the sheath 13 abuts against the end of the cervix. The catheter 11 is then threaded through the sheath 13 to position the balloon 20 in the cervical canal, or just past the cervical canal inside the uterine cavity of the uterus (FIG. 3A).

The syringe 12 of the apparatus 10, which is filled with a diagnostic fluid such as saline or a contrast dye, is then operated to inject the diagnostic fluid into the uterine cavity of the uterus. The fluid pressure generated within the lumen 21 by the operation of the syringe 12 causes the first slit 22 at the distal end 17 of the catheter body 16 to open and allow the diagnostic fluid to flow from the catheter 11 into the uterine cavity of the uterus. At the same time as the uterus is being filled with the fluid, back-pressure within the lumen 21 of the catheter 11 caused by restricted fluid flow through the first slit 22 causes the second slit 23 to open to allow fluid to enter and inflate the balloon 20, thus preventing leakage of fluid through the cervical canal.

Once the balloon 20 is inflated, the slits 22, 23 operate as check valves by automatically closing to prevent the balloon 20 from deflating. The inflated balloon 20 locks the position of the apparatus 10 and seals the uterine cavity to prevent leakage of the diagnostic fluid therefrom. Radiography or sonography can then be performed to provide imaging information pertaining to the subject uterus or fallopian tubes.

When it is desirable to deflate the balloon 20, the syringe 12 is uncoupled from the catheter 11 and the catheter is withdrawn slightly through the cervix. This causes the muscular tissue of the cervix to compress the balloon 20 slightly thus forcing the fluid in the balloon back into the lumen 21 of the catheter 11 through the slit 23. Once the balloon 20 is deflated, the catheter 11 of the apparatus 10 can be fully withdrawn from the uterus through the cervical canal.

While the foregoing invention has been described with reference to the above embodiments, various modifications and changes can be made without departing from the spirit of the invention. Accordingly, all such modifications and changes are considered to be within the scope of the appended claims.

What is claimed is:

1. A catheter useful for non-surgical entry into a uterus to dispense a diagnostic fluid therein, the catheter comprising:

a tubular body having a single lumen extending from a first end thereof to a second end thereof, the lumen having an external opening adjacent the first end configured for dispensing a diagnostic fluid into the interior of a subject uterus; and a balloon disposed marginally adjacent to the first end of the body for fluid sealing the interior of the subject uterus;

the lumen having a second opening in fluid communication with the interior of the balloon for inflation thereof with the diagnostic fluid;

wherein the external opening adjacent the first end generates a back-flow within the lumen which causes the fluid to enter and inflate the balloon through the second opening;

wherein the balloon can be sequentially inflated into first and second predetermined shapes;

wherein the first predetermined shape is substantially elliptical and the second predetermined shape is substantially spherical wherein the external opening and the second opening operate as check valves by automatically closing to prevent the balloon from deflating.

2. A catheter apparatus useful for non-surgical entry into a uterus to dispense a diagnostic fluid therein, the catheter apparatus comprising:

a catheter;

a syringe for delivering the diagnostic fluid into the catheter;

the catheter having a balloon disposed marginally adjacent to a first end thereof for fluid sealing the interior of the subject uterus, a single lumen extending from the first end to a second end of the catheter, the lumen having an external opening adjacent the first end configured for dispensing the diagnostic fluid into the interior of a subject uterus and a second opening in fluid communication with the interior of the balloon for inflation thereof with the diagnostic fluid;

wherein the external opening adjacent the first end generates a back-flow within the lumen which causes the fluid to enter and inflate the balloon through the second opening;

wherein the balloon can be sequentially inflated into first and second predetermined shapes; and wherein the first predetermined shape is substantially elliptical and the second predetermined shape is substantially spherical wherein the external opening and the second opening operate as check valves by automatically closing to prevent the balloon from deflating.

* * * * *